United States Patent [19]

Jackson

[11] 4,381,267
[45] Apr. 26, 1983

[54] AIRWAY HUMIDIFIER FOR THE RESPIRATORY TRACT

[76] Inventor: Richard R. Jackson, One Atlantic Ave., Swampscott, Mass. 01907

[21] Appl. No.: 267,867

[22] Filed: May 28, 1981

Related U.S. Application Data

[63] Continuation-in-part of Ser. No. 46,943, Jun. 8, 1979, abandoned, which is a continuation-in-part of Ser. No. 923,905, Jul. 12, 1978, abandoned.

[51] Int. Cl.³ ............................................. A61M 15/00
[52] U.S. Cl. ................................ 261/104; 128/204.13; 261/DIG. 65
[58] Field of Search ................. 261/104, 107, 152–155, 261/157, 161, DIG. 65; 159/DIG. 27, DIG. 28; 55/16, 158, 159; 210/22 R, 22 A, 22 B, 321.4, 210/321.1, 321.2, 436, 500.2, 640, 644, 650; 128/192, 128/212, 203.15, 203.16, 204.13

[56] References Cited

U.S. PATENT DOCUMENTS

| | | | |
|---|---|---|---|
| 3,186,941 | 6/1965 | Skiens | 210/638 |
| 3,228,877 | 1/1966 | Mahon | 210/22 R |
| 3,339,341 | 9/1967 | Maxwell et al. | 55/16 |
| 3,342,729 | 9/1967 | Strand | 159/DIG. 27 |
| 3,373,876 | 3/1968 | Stewart | 210/321 B |
| 3,423,481 | 1/1969 | McLain et al. | 210/321 A |
| 3,616,796 | 11/1971 | Jackson | 261/104 |
| 3,772,072 | 11/1973 | Brown et al. | 210/500 M |
| 3,803,810 | 4/1974 | Rosenberg | 55/159 |
| 3,871,373 | 3/1975 | Jackson | 261/104 |
| 3,905,905 | 9/1975 | O'Leary et al. | 210/436 |
| 3,912,795 | 10/1975 | Jackson | 261/104 |
| 4,010,748 | 3/1977 | Dobritz | 261/104 |
| 4,031,012 | 6/1977 | Gics | 55/158 |
| 4,075,100 | 2/1978 | Furuta et al. | 210/321 A |
| 4,086,305 | 4/1978 | Dobritz | 261/104 |
| 4,098,852 | 7/1978 | Christen et al. | 261/104 |
| 4,146,597 | 3/1979 | Eckstein et al. | 128/204.13 |
| 4,155,961 | 5/1979 | Benthin | 261/104 |

FOREIGN PATENT DOCUMENTS

| | | | |
|---|---|---|---|
| 2617985 | 10/1977 | Fed. Rep. of Germany | 261/104 |
| 1445549 | 6/1966 | France | 210/321 R |
| 1455991 | 9/1966 | France | 210/321 R |
| 1465852 | 1/1967 | France | 210/321 R |
| 2267138 | 12/1975 | France | 210/321 R |
| 1221625 | 2/1971 | United Kingdom | 55/159 |

*Primary Examiner*—Tim R. Miles

[57] ABSTRACT

According to the present invention, an airway humidifier for directly humidifying the air flow requirement of a respiratory tract during the inspiration phase of a breathing cycle is provided, which comprises a nest of relatively large bore, thin wall air transmitting elongated hollow fibers terminating at an output end that is adapted to communicate the merged flow through a tube to the respiratory tract, a water chamber surrounding said fibers and having sufficient rigidity to resist collapse when subjected to negative operational water pressure, a water source for water heated to about 105° F. (40° C.) and a water pump connected to said chamber and said source and adapted to maintain said chamber filled with water under negative pressure, said fibers having an internal diameter of the order of 0.050 inch, and being present in sufficient number and length to enable the peak air flow rate of said requirement to proceed through said nest with a characteristic pressure drop of less than 5 centimeters of water, the walls of said fibers having a wettable surface and under said negative pressure water conditions being permeable to water vapor and impermeable to liquid water, and the aggregate wetted surface area of said fibers being sufficient to humidify the peak flow rate of said requirement of said respiratory tract, whereby pulsing air flow into the respiratory tract can be humidified by a compact, closely-located unit.

16 Claims, 7 Drawing Figures

AIRWAY HUMIDIFIER FOR THE RESPIRATORY TRACT

This application is a continuation-in-part of my co-pending application U.S. Ser. No. 046,943 filed June 8, 1979, now abandoned which in turn is a continuation-in-part of application Ser. No. 923,905, filed July 12, 1978, now abandoned,

BACKGROUND OF THE INVENTION

This invention relates to an airway humidifier for humidifying and delivering gases such as air or oxygen via a tube directly to a patient or other person needing breathing support.

In humidifiers used today, the air is typically overheated up to 50° to 60° C., and the cooling of the air as it proceeds to the person's airway depends on many factors, e.g. room temperature, length of the tube from the humidifier to the person, minute volume etc. Therefore, the temperature reaching the sensitive tissue of the airway is not well controlled. Often moisture is condensed in the tube leading to the patient and creates an accumulation that can cause harm. Furthermore, in present-day humidifiers there is direct contact between air and liquid water which is hygienically undesirable.

The invention constitutes an improvement over my prior patents U.S. Pat. Nos. 3,616,796; 3,871,373; 3,912,795 and to later efforts of Dobritz, U.S. Pat. Nos. 4,010,748 and 4,086,305. According to my prior patents, a new general type of airway humidifier for the respiratory tract is provided which operates according to the diffusion principle in which water vapor from a water supply permeates a wall or membrane and enters a stream of breathing air while the water supply is maintained separate from the air stream by the wall. Such a di-fusion humidifier offers a number of potential advantages over other methods of humidification, but no satisfactory form for its manufacture has yet been realized. The present invention fulfills this need.

SUMMARY OF THE INVENTION

According to the present invention, an airway humidifier for directly humidifying the air flow requirement of a respiratory tract during the inspiration phase of a breathing cycle is provided, which comprises a nest of relatively large bore, thin wall air transmitting elongated hollow fibers terminating at an output end that is adapted to communicate the merged flow through a tube to the respiratory tract, a water chamber surrounding said fibers and having sufficient rigidity to resist collapse when subjected to negative operational water pressure, a water source for water heated to about 105° F., and a water pump connected to said chamber and said source and adapted to maintain said chamber filled with water under negative pressure, said fibers having an internal diameter of the order of 0.050 inch, and being present in sufficient number and length to enable the peak air flow rate of said requirement to proceed through said nest with a characteristic pressure drop of less than 5 centimeters of water, the walls of said fibers having a wettable surface and under said negative pressure water conditions being permeable to water vapor and impermeable to liquid water, and the aggregate wetted surface area of said fibers being sufficient to humidity the peak flow rate of said requirement of said respiratory tract, whereby pulsing air flow into the respiratory tract can be humidified by a compact, closely-located unit.

Pursuant to the invention, the fibers divide the pulses of dry inhalation air (here the word "air" is intended to include pure or diluted oxygen) for the person, into a multiplicity of parallel air-flow filaments. These pulsing filaments of flow are humidified by water vapor that permeates walls of the fibers in a flow of vapor that is opposite to the pressure differential across the fibers, the wettable nature of the fibers cooperating to enable such vapor transmission; simultaneously this pressure differential. Thus, the pulsing air flow requirement of the respiratory tract can be humidified by a practical, compact and lightweight device that is disposed close to the mouth of the person and which operates essentially at body temperature.

Thus, the pulsing air flow requirement of the respiratory tract can be humidified by a practical, compact and lightweight device that is disposed close to the mouth of the person and which operates essentially at body temperature.

In preferred embodiments under operating conditions the fibers of the humidifier have a water vapor transmission characteristic of about 45 milligrams of water vapor for each liter per minute of peak air flow requirement, the airway humidifier adapted for the human adult has a characteristic flow rate of about 60 liters per minute at a pressure drop of 3 cm of water; the airway humidifier adapted for children has a characteristic flow rate of about 10 liters per minute at a pressure drop of 2 cm of water; the fibers are very thin walled, e.g. the fibers have a wall thickness that is 10 percent or less of the internal diameter of said fibers, preferably of the order of 0.005 inch or less and preferably about 0.003 inch; as adapted to meet the flow requirement of the adult-human, the fibers define an aggregate effective water-vapor transmitting surface area of the order of about one half square foot; there are less than 350 fibers, preferably down to 200 or fewer fibers in the humidifier; the fibers have an effective length of the order of 10 centimeters or preferably substantially less; the substance of said fibers incorporates a wetting agent; said wetting agent is glycerine or dioctyle sodium sulfo succinate; the substance of said fibers is selected from the group consisting of polysulfones and acrylic copolymers; the humidifier includes means sized for connection of its inlet end to the hose of a respirator and its outlet end to a breathing tube connected to the airway of a person and adapted to humidify air pulses from the respirator and deliver the humidified air to the respiratory tract at about body temperature; the humidifier comprises a disposable tubular component of a breathing circuit; and the airway humidifier includes a relief valve connected to the water side of said unit, constructed to respond to the occurrence of positive water pressure surrounding the fibers to automatically vent said water to the atmosphere to prevent positive pressure build-up in the water surrounding the fibers, whereby said humidifier can provide full humidification of air directed into a person in a fail-safe manner without risk of flow of liquid into the bore of said fibers in the event of fiber leak.

The invention simultaneously meets the many different needs that have not together been previously met for an airway humidifier through which life-supporting air is channeled. The humidifier successfully provides low air-flow resistance, so low that the patient can breathe through the humidifier without assistance; it avoids any substantial risk that the patient might inhale large volumes of gross (i.e. liquid) water; it achieves small size and lightweight for convenience and to avoid introducing a large compressible air volume in the path and to enable placement close to the mouth, for example, as a tubular component of a breathing circuit; it has a long shelf life; it is of simple and rugged construction and of such low cost as to be disposable; and it provides improvement in overall operation.

FURTHER PRIOR ART COMMENT

Hollow fibers with walls of water-permeable substance have been used for many years in filters and the like, see e.g. U.S. Pat. Nos. 3,228,877; 3,339,341 and 3,342,729. In the context of a heat exchanger, U.S. Pat. No. 4,098,852 has suggested to condition or humidify air by use of air-carrying fibers and positive pressure. Small-bore water-filled fibers under positive pressure have also been suggested for humidifying air, U.S. Pat. No. 4,155,961 (German OS No. 2,617,985, and see U.S. Pat. No. 4,010,748). Negative pressure operation of a broad area membrane humidifier has been known for some time (see U.S. Pat. Nos. 3,616,796 and Dobritz 4,086,305). Despite all of the above, the prior art has not taught the present invention nor suggested the important combination and cooperation of features necessary to enable its realization.

DRAWINGS

FIG. 2 is a transverse cross-sectional view of the embodiment taken on line 2—2 (omitting the fibers) and showing a closed mushroom valve in cross-section, while

DESCRIPTION OF PREFERRED EMBODIMENT

Figure 1:
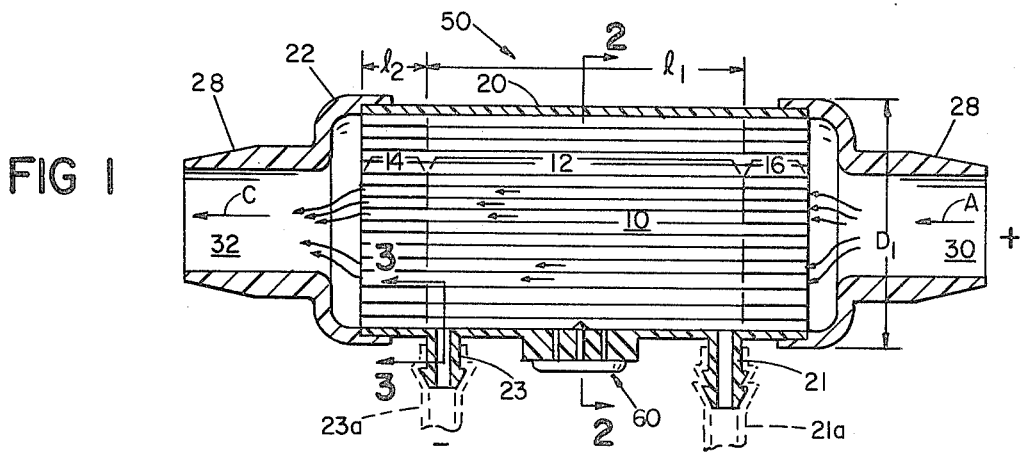
FIG. 1 is a longitudinal cross-sectional view of the preferred embodiment.

Referring to FIGS. 1–4 the medical humidifier 50 comprises a bundle 10 of straight, elongated fibers, made of a wettable substance (glycerinized polysulfone) which is permeable to water vapor and impermeable to water under the conditions utilized (negative pressure). The fiber bundle is loosely arranged in its major midportion 12 to provide water flow passages 13 (FIGS. 3 and 4) over the exterior of the fibers, while the end portions 14 and 16 of the bundle are potted (bonded together) in water-impermeable bonding material 18 (epoxy). Similarly the sides of the potted end portions 14, 16 are joined to end portions of chamber 20 defined by a rigid cylindrical wall (high density polystyrene). Between these ends the housing defines a water chamber capable of withstanding negative pressure. End caps 22 and 24 are provided at the respective ends of the housing, terminating in tapered external member 28. These serve as standard male breathing circuit connectors for insertion into mating female connectors or hose.

Figure 5:
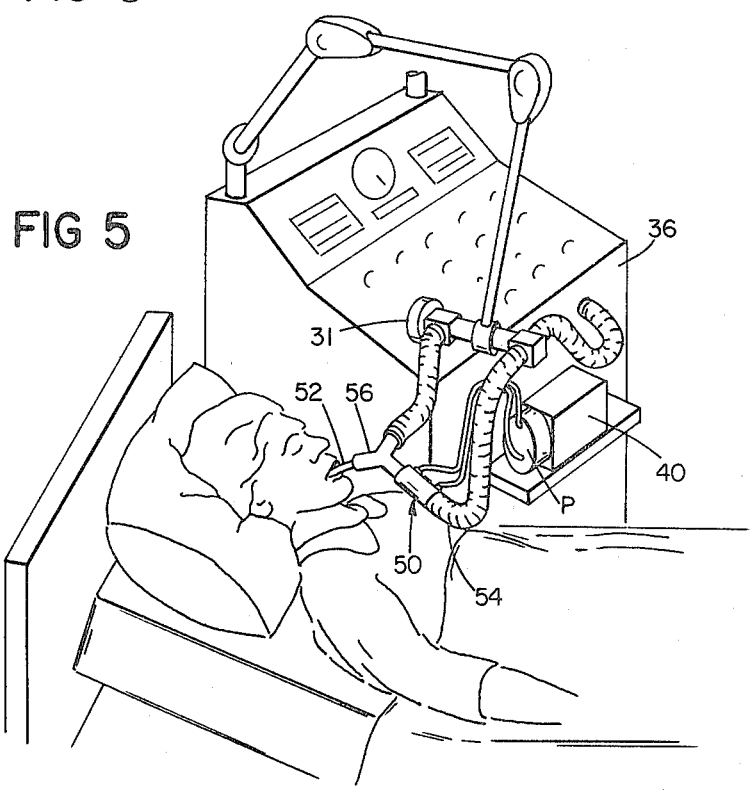
FIG. 5 is a perspective view showing the embodiment in use with a patient.

The humidifier unit is connected in any suitable respiratory flow path. In FIG. 5 the humidifier is shown in the inhalation leg from the respirator to a patient, with a respirator controlled exhalation valve 31 at the end of a Y connector exhausting to ambient.

As shown in FIG. 1, the end caps 22 and 24 each provide open spaces 30 and 32 beyond the ends of the fiber bundle, to define inlet and outlet air plenums. Air from the respirator 36 in FIG. 5 enters the male connector 28 at FIG. 1 at the right hand side, fills inlet air plenum 30 and is there distributed across the end face of the fiber bundle, where it splits, to enter the numerous hollow fibers as filaments of air flow. These proceed through the fibers under the pressure of the respirator, exiting into outlet air plenum 32 on the left hand side of FIG. 1 where they rejoin. The unified flow proceeds through the connector to the patient.

Figure 6:
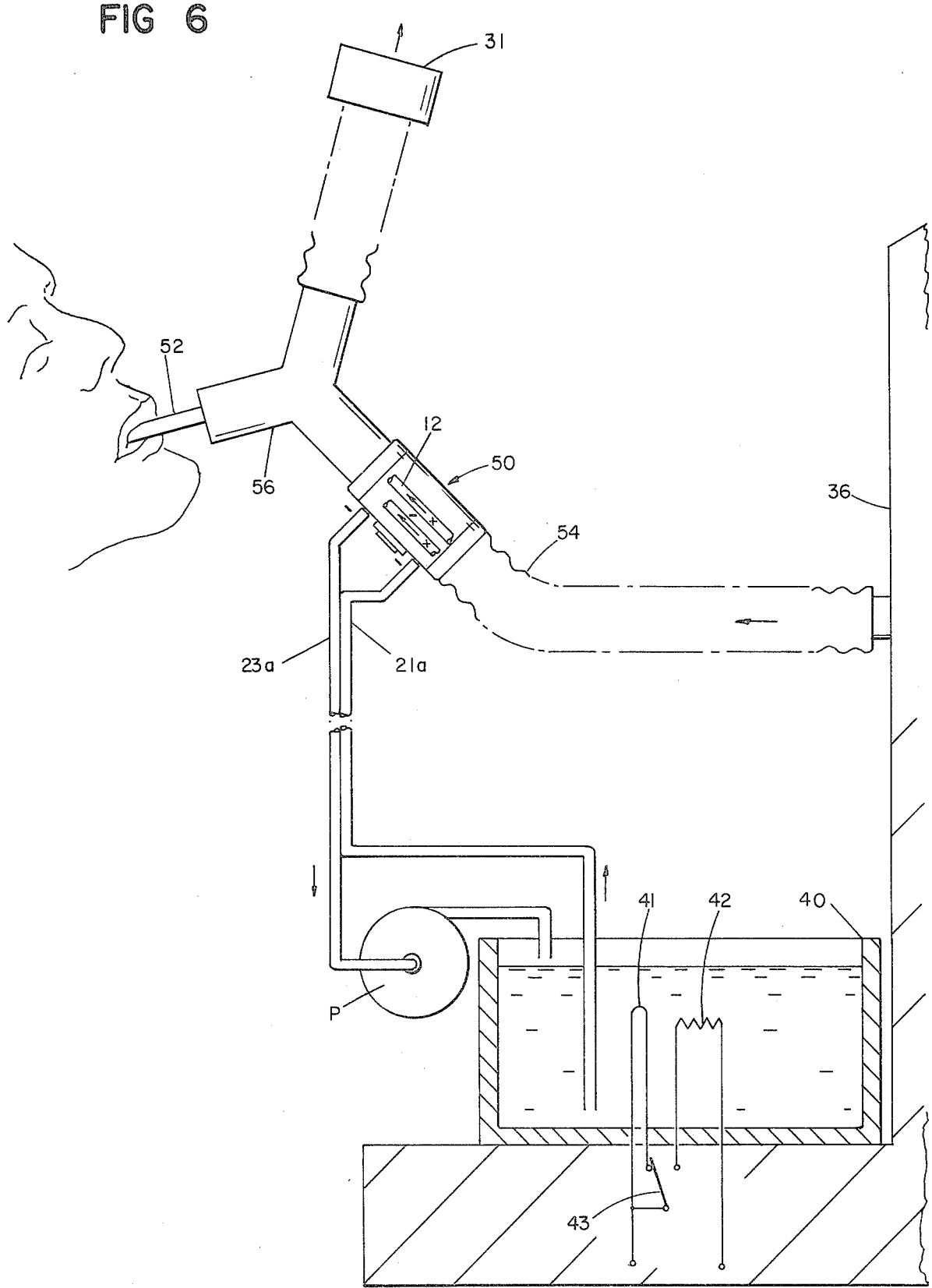
FIG. 6 is a diagrammatic view of the flow arrangement for air to be humidified and the negative pressure water.

The water chamber 20 has water inlet and outlet connectors 21, 23 (of different configuration to avoid mix-up) at the right and left hand sides of FIG. 1 respectively. These connectors and the conduits, 21a, 23a are also of sufficiently rigid material to withstand negative pressure. Inlet conduit 21a extends to a water reservoir 40 (FIG. 6) where the end is submerged in water. A heater element 42 maintains the water at the desired temperature (105° F.) under the control of probe 41 and thermostatic control switch 43. The water outlet conduit 23a is connected to the inlet of discharge pump P which discharges excess water into the reservoir 40. Water is drawn by the pump through the inlet 21a and through the space between the loosely nested fibers, thus filling the entire free volume of chamber 20 with water under negative pressure, e.g. minus 2 psig, i.e. the absolute pressure is 2 psi less than the pressure of the atmosphere. The water is drawn through discharge conduit 23a under the pull of discharge pump P.

Figure 2:
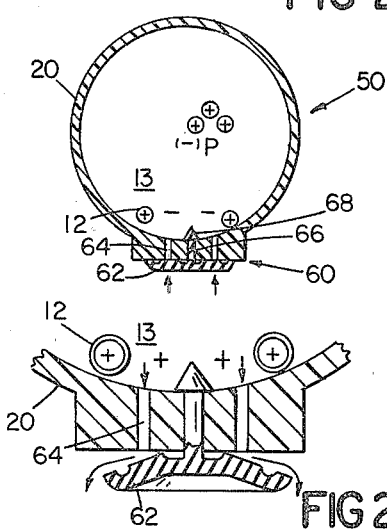
Figure 2A:
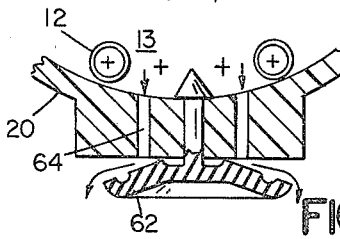
FIG. 2a is a view of the mushroom valve when open.

A positive pressure relief valve 60 (FIG. 2) may be incorporated in the wall of the housing. As shown in FIGS. 2 and 2a, this valve is of the so-called, well-known mushroom type. It comprises a leaflet 62 overlying relief holes 64 which extend from the interior of the chamber 20 to the atmosphere. A stem 66 is integrally joined to leaflet 62 and ends in enlarged inward end 58 which is larger than the passage through which the stem 62 extends and therefore holds the leaflet in place. Under negative water pressure conditions as shown in FIG. 2 the leaflet seals the passages 64. However, referring to the magnified view of FIG. 2a, in the event that positive pressure should accidently be applied to the water volume of chamber 20, this positive pressure acts through the passage 64 to deflect the leaflet 62 to allow escape of liquid until the positive pressure is relieved.

The fibers have internal diameter of 0.060 inch and wall thickness of 0.005 in. They are glycerinized to make them hydrophylic by being immersed in glycerine before being dry.

The fibers are 3 inches in length with ⅜ to ½ inch of each end sealed in the potting material, resulting in an effective vapor-transmitting length between the ends in the range of 2 and 2¼ inch.

In this embodiment 178 of the fibers are nested together and provide an aggregate vapor transmitting area in the range of 67 to 84 in$^2$, depending upon the length of the potted end regions, and a capacity to humidify ambient air to saturation at 98.6° F. at peak air flow rates between about 85 and 95 liters/min with a pressure drop of 3 cm of water.

The flow resistance of this nested fiber module can in a very general way be represented by the figure of merit value $$R = L/D^4 \times 1/N = 1300$$

where L is the air transmitting (overall) length of the fibers in inches, D is the internal diameter of the fibers in inches and N is the number of fibers.

This figure of merit value (though only a gross indicator of the order of magnitude of flow resistance) does reflect a significant difference of the present invention from other fiber modules that are subjected to pulsing air flow conditions.

In another adult sized humidifier 200 hydrophylic polysulfone fibers are employed, with internal fiber diameter of 0.050 inch, external diameter of 0.055 inch, 7 cm overall fiber length, 6 cm effective vapor transmitting length, and 72 in$^2$ effective surface area. This unit has an R value of 2200 and at air flow rate of 60 liters per minute, has a characteristic air pressure drop of 2.7 centimeters of water.

The humidifier can be placed in any of the variety of respirator circuits and flow paths and indeed the patient can spontaneously inhale through it with no assistance of a respirator.

Suitable air flow characteristics in a practical, compact module are achievable with fibers of internal diameter of the order of 0.050 inch (up to about 0.080 inch id). The length of the fibers is dependent upon their diameter and upon the number N of the fibers to be employed. The number N is also dependent upon the specific vapor transmitting characteristic of the particular fiber material and wall thickness selected. In general, for the adult-sized humidifier the number of fibers will be less than 350, down to 200 or less, the length of the nest of fibers will be less than 10 cm and the wall thickness of the fibers will be less than 10% of the internal diameter of the fibers, generally less than 0.005 inch, and the vapor transmission area will be of the order of ½ square foot or less. The air pressure drop will be less than 5 in. of water across the unit, preferably less than 3 cm of water at a peak flow rate of 60 liters per minute for the adult.

For units constructed for children, because of the lower peak flow requirement, the capacity of the unit can be made correspondingly less, e.g. of 10 liters per minute peak flow rate at a pressure drop of less than 2 centimeters of water. This enables corresponding adaptation of one or more of the parameters as desired. In general, the unit will be constructed to transmit water vapor at the rate of 45 milligrams per liter per minute for each liter of air per minute of the design requirement, and to produce an air pressure drop preferably of less than 3 cm H$_2$O at the designed flow requirement for the adult and less than 2 cm H$_2$O for young children.

The glycerinized fibers have the advantage of high vapor rate transmission and long dry shelf life and when used with the positive pressure relief valve, offer a fail-safe operation. Where it is desired to provide safety in another way, it is possible to use fibers which are more immune to transmission of liquid water even in the event of accidental application of positive pressure to the water chamber. In this case preferably the fibers are produced to the dry stage as hydrophobic polysulfone fibers and are subsequently treated with a wetting agent as dioctyl sodium sulfo succinate (stool softener marketed by Mead Johnson) and/or with glycerine. The same can be done if the fibers are formed of acrylic co-polymers such as the XM formulation manufactured by Amicon Corporation.

The water chamber 20 can advantageously be formed by injection molding of any suitable rigid plastic used in medical appliances, for instance the high impact polystyrene, mentioned above. The end caps, including the connectors, and defining the air plenums, can be of the same or similar material and can for instance be solvent-bonded to the exterior of the housing 20 in the manner shown. In a typical construction the assembly of fibers, having a length longer than the housing, is inserted loosely in the housing, with potting material, epoxy or others such as silicone rubber, filling the space between adjacent fibers in the end regions. After the potting material is set, the extreme ends of the matrix of potting material and hollow fibers can be sliced, as with a knife, flush with the ends of the housing 20, to provide a smooth end face with the fiber ends open to transmit air. The resulting bundle of fibers can readily provide a diffusion wall surface area of the order of 0.5 square feet, effective to humidify an aggregate air flow rate of the order of 60 liters per minute at the instant of peak flow during the respirator cycle.

OPERATION

Figure 3:
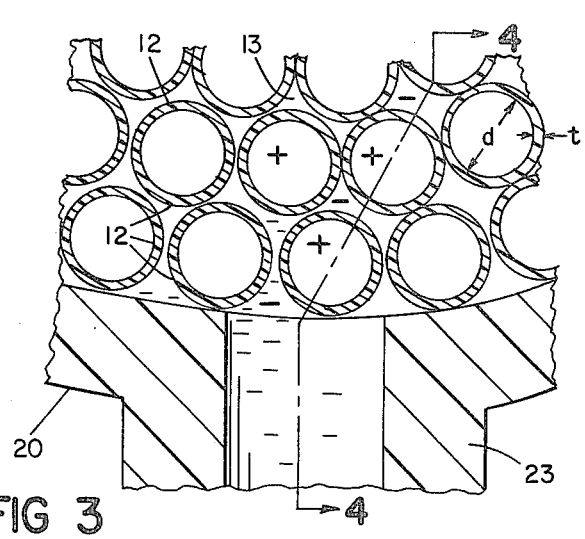
FIG. 3 is a partial transverse cross-sectional view taken on line 3—3 of FIG. 1, on a magnified scale.
Figure 4:
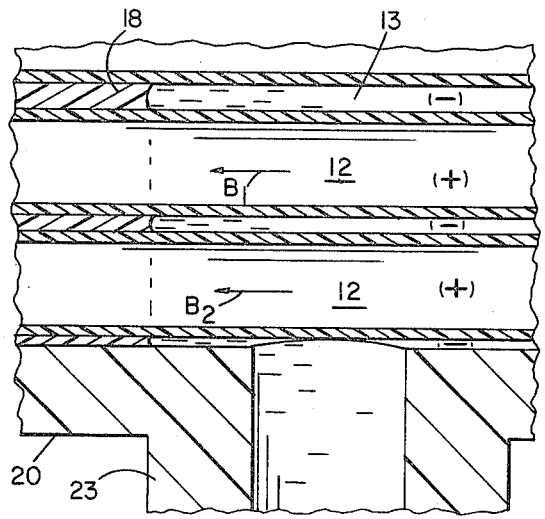
FIG. 4 is a longitudinal cross-sectional view on magnified scale taken on line 4—4 of FIG. 3.

Referring to the figures the gross pulse of inlet air A, FIG. 1, from the respirator 36 (FIG. 6) at the inspiration phase of successive breathing cycles is divided into air stream filaments $B_1$, $B_2$, etc. in FIGS. 3 and 4 by the many fibers of the nest. The heated water, as indicated diagrammatically in FIGS. 3 and 4, flows over the exterior of these fibers while water vapor produced by this water supply permeates the thin walls of the fibers, in opposition to the pressure differential, and humidifies the dry air filaments. The air stream filaments $B_1$, $B_2$, etc. after transiting the length of the fibers 12 are humidified to saturation at body temperature. The air filaments are then restored to a unified air flow C in the discharge plenum 32, which proceeds into the patient.

In a typical operation the respirator 36 of FIG. 5 operates as an open cycle system in which exhaled air is discharged to the atmosphere through exhalation valve 31. During the inspiration phase of the cycle the respirator gradually increases the pressure on conduit 54, supplying air through the humidifier 50 to the end of endotracheal tube 52 inserted into the airway of the patient. The valve 31 in the discharge leg 56 of the Y fitting is closed during this phase by a control line from the respirator, hence all air flow from the respirator is channeled through the humidifier 50 and into the patient. During the expiration phase the patient exhales spontaneously. At this time valve 31 is released by the control line from the respirator to relieve the exhaled air to the atmosphere. A check valve, not shown, during the expiration phase prevents back-flow of exhaled air through the humidifier.

The hollow fibers being subjected to a decreasing pressure gradient from inside to outside take advantage of the substantial tensile strength of the wall of the fibers, and do not collapse. With the water under vacuum, little liquid water will enter the airway in the event of accidental rupture of a fiber wall. Even if a reverse pressure differential is encountered as by accidental misconnection of the pump, it is important to realize that the hollow fibers, due to their small size, demonstrate a sufficient degree of structural rigidity to resist total crushing that would totally block the air flow to the patient.

By use of the particular fibers described, a sufficient vapor-transmitting surface area to volume ratio is obtained while still obtaining sufficient air-transmitting capacity to enable a small number of fibers, less than 350, preferably down to 200 and below, to be employed for the adult humidifier. The feature permits a large diffusion surface to be obtained in a small geometric volume. Such small size permits it to be an inexpensive disposable component, to be replaced periodically, for instance once a day, at the same time that the hoses are ordinarily changed. The construction leads to the possibility of extending the time between sterilizations of the inlet hose, from the respirator to the humidifier, owing to the fact that it now does not contain moist warm air and therefore is not a place where bacteria multiply rapidly.

Further improvements, employing the principles of the present invention, and dealing wilth more specific details for an optimum unit for a particular application are within the claims.

What is claimed is:

1. An airway humidifier for directly humidifying the air flow requirement of a respiratory tract of a living being breathing directly through the humidifier during the inspiration phase of a breathing cycle, said humidifier comprising a nest comprising a large multiplicity of relatively large bore, thin-walled-air-transmitting elongated hollow fibers terminating at an output end that is adapted to communicate the merged flow through a tube to the respiratory tract, said fibers having an internal diameter of the order of 0.050 inch, up to about 0.080 inch, and being present in sufficient number and length to enable the peak air flow rate of said air flow requirement to proceed through said nest with a characteristic pressure drop of less than 5 centimeters of water, a water chamber surrounding said fibers and having sufficient rigidity to resist collapse when subjected to negative operational water pressure, a water source for water heated to about 105° F., and a water pump connected to exhaust said chamber, said water chamber connected to said water source whereby said pump is adapted to maintain said chamber filled with water under negative pressure by drawing water through said chamber from said source, said fibers incorporating a wetting agent whereby the walls of said fibers having a wettable surface and under said negative pressure water conditions being permeable to water vapor and impermeable to liquid water, and the aggregate wetted surface area of said fibers being sufficient to humidify the peak flow rate of said air flow requirement of said respiratory tract, whereby pulsing air flow into the respiratory tract can be humidified by a compact, closely-located unit.

2. The airway humidifier of claim 1 wherein under operating conditions said fibers have a water vapor transmission characteristic of about 45 milligrams of water vapor for each liter of peak air flow requirement.

3. The airway humidifer of claim 2 adapted for the human adult having a characteristic flow rate of about 60 liters per minute at a pressure drop of 3 cm of water.

4. The airway humidifier of claim 2 adapted for children having a characteristic flow rate of about 10 liters per minute at a pressure drop of 2 cm of water.

5. The airway humidifier of claim 1 wherein said hollow fibers have a wall thickness that is 10 percent or less of the internal diameter of said fibers.

6. The airway humidifier of claim 5 wherein said hollow fibers have a wall thickness of less than 0.005 inch.

7. The airway humidifier of claim 5 adapted to meet the flow requirement of the adult human, wherein said fibers define an aggregate effective water-vapor transmitting surface area of less than about one half square foot.

8. The airway humidifier of claim 1 wherein said wetting agent is glycerine.

9. The airway humidifier of claim 1 wherein said wetting agent is dioctyl sodium sulfo succinate.

10. The airway humidifier of claim 1 wherein the substance of said fibers is selected from the group consisting of polysulfones and acrylic copolymers.

11. The airway humidifier of claim 1 wherein there are less than 350 fibers in the humidifier.

12. The airway humidifier of claim 11 wherein said fibers have an effective length of the order of 10 centimeters or less.

13. The airway humidifier of claim 1 including a relief valve connected to the water side of said unit, constructed to respond to the occurrence of positive water pressure surrounding the fibers to automatically vent said water to the atmosphere to prevent positive pressure build-up in the water surrounding the fibers, whereby said humidifier can provide full humidification of air directed into a person in a fail-safe manner without risk of flow of liquid into the bore of said fibers in the event of fiber leak.

14. The airway humidifier of claim 1 including means sized for connection of its inlet end to the hose of a respirator and its outlet end to a breathing tube leading to the airway of a person, said humidifier adapted to humidify pulses of air received from the respirator and deliver humidified air to the respiratory tract at about body temperature.

15. The airway humidifier of claim 1 comprising a disposable tubular component of a breathing circuit.

16. The humidifier of claim 1 characterized in that said bundle of fibers has an aggregate air flow figure of merit resistance value R of about 1300 where $$R = L/D^4 \times 1/N$$

L and D are length and internal diameter of fibers in inches, and N is the number of fibers.

* * * * *